United States Patent

Christie et al.

[11] Patent Number: 5,089,024
[45] Date of Patent: Feb. 18, 1992

[54] MULTI-FOCAL INTRAOCULAR LENS

[75] Inventors: Bruce A. Christie, Newport-Richey; Gary L. Guenthner, Largo, both of Fla.; J. Warren Blaker, Bronx, N.Y.

[73] Assignee: Storz Instrument Company, St. Louis, Mo.

[21] Appl. No.: 183,202

[22] Filed: Apr. 19, 1988

[51] Int. Cl.$^5$ ............................................. A61F 2/16
[52] U.S. Cl. ........................................ 623/6; 351/161; 351/171
[58] Field of Search ............ 623/6; 351/160 R, 160 H, 351/161, 168, 171, 172

[56] References Cited

U.S. PATENT DOCUMENTS

| | | |
|---|---|---|
| 1,518,405 | 12/1924 | Glancy . |
| 2,878,721 | 3/1959 | Kanolt . |
| 3,034,403 | 5/1962 | Neefe . |
| 3,270,099 | 8/1966 | Camp . |
| 3,339,997 | 9/1967 | Wesley . |
| 3,458,870 | 8/1969 | Stone, Jr. . |
| 3,555,126 | 1/1971 | Gitson . |
| 3,614,217 | 10/1971 | Bronstein . |
| 3,711,870 | 1/1973 | Deitrick . |
| 3,726,587 | 4/1973 | Kendall . |
| 3,794,414 | 2/1974 | Wesley . |
| 3,913,148 | 10/1975 | Potthast . |
| 3,950,082 | 4/1976 | Volk . |
| 4,010,496 | 3/1977 | Neefe . |
| 4,118,853 | 10/1978 | Mignen . |
| 4,172,297 | 10/1979 | Schlegel . |
| 4,174,156 | 11/1979 | Glorieux . |
| 4,206,518 | 6/1980 | Jardon et al. . |
| 4,253,199 | 3/1981 | Banko . |
| 4,254,509 | 3/1981 | Tennant . |
| 4,315,673 | 2/1982 | Guilino et al. . |
| 4,316,293 | 2/1982 | Bayers . |
| 4,338,005 | 7/1982 | Cohen . |
| 4,365,360 | 12/1982 | Ong . |
| 4,377,329 | 3/1983 | Poler . |
| 4,402,579 | 9/1983 | Poler . |
| 4,412,359 | 11/1983 | Myers . |
| 4,418,431 | 12/1983 | Feaster . |
| 4,418,991 | 12/1983 | Breger . |
| 4,435,856 | 3/1984 | L'Esperance . |
| 4,466,705 | 8/1984 | Michelson . |
| 4,477,158 | 10/1984 | Pollock et al. . |
| 4,504,982 | 3/1985 | Burk . |
| 4,512,040 | 4/1985 | McClure . |
| 4,514,061 | 4/1985 | Winthrop . |
| 4,525,043 | 6/1985 | Bronstein . |
| 4,564,484 | 1/1986 | Neefe . |
| 4,573,998 | 3/1986 | Mazzocco . |
| 4,575,373 | 3/1986 | Johnson . |
| 4,580,882 | 4/1986 | Nuchman et al. . |
| 4,593,981 | 6/1986 | Scilipoti . |
| 4,605,409 | 8/1986 | Kelman . |
| 4,619,657 | 10/1986 | Keates et al. . |
| 4,636,211 | 1/1987 | Nielsen et al. . |
| 4,637,697 | 1/1987 | Freeman . |
| 4,640,593 | 2/1987 | Shinohara . |
| 4,642,112 | 2/1987 | Freeman . |
| 4,655,565 | 4/1987 | Freeman . |
| 4,702,573 | 10/1987 | Morstad . |
| 4,710,193 | 12/1987 | Volk . |
| 4,710,197 | 12/1987 | Donn et al. . |
| 4,720,286 | 1/1988 | Bailey et al. . |
| 4,752,123 | 6/1988 | Blaker . |
| 4,795,462 | 1/1989 | Grendahl ................................ 623/6 |
| 4,813,955 | 3/1989 | Achatz et al. ........................... 623/6 |
| 4,898,461 | 2/1990 | Portney ............................ 351/161 X |

FOREIGN PATENT DOCUMENTS

| | | |
|---|---|---|
| 3332313 | 4/1985 | Fed. Rep. of Germany .......... 623/6 |
| 1103399 | 12/1955 | France . |
| WO86/03961 | 7/1986 | PCT Int'l Appl. ..................... 623/6 |
| 939016 | 10/1963 | United Kingdom . |

OTHER PUBLICATIONS

J. Warren Blaker, "Modern Lens Design for Today & Tomorrow", break-out session: Amer. Society of Cataract & Refractive Surgery—Seminar, Apr. 9, 1986.

Primary Examiner—Ronald Frinks
Attorney, Agent, or Firm—Brooks & Kushman

[57] ABSTRACT

An intraocular lens, for use within the human eye, contains three concentric regions. An innermost region provides far-field vision. A middle region, surrounding the innermost region, provides near-field vision. An outermost region, surrounding the middle region, provides far-field vision. The intermost region is of a size such that, when the pupil constricts in bright light, the innermost region remains exposed to incoming light, and can thus focus distant images in bright light.

2 Claims, 4 Drawing Sheets

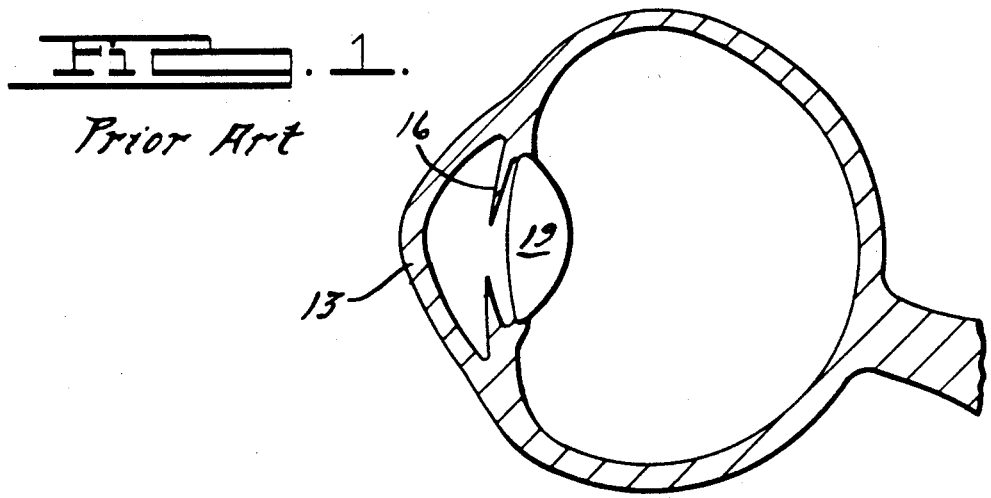
FIG. 1. Prior Art
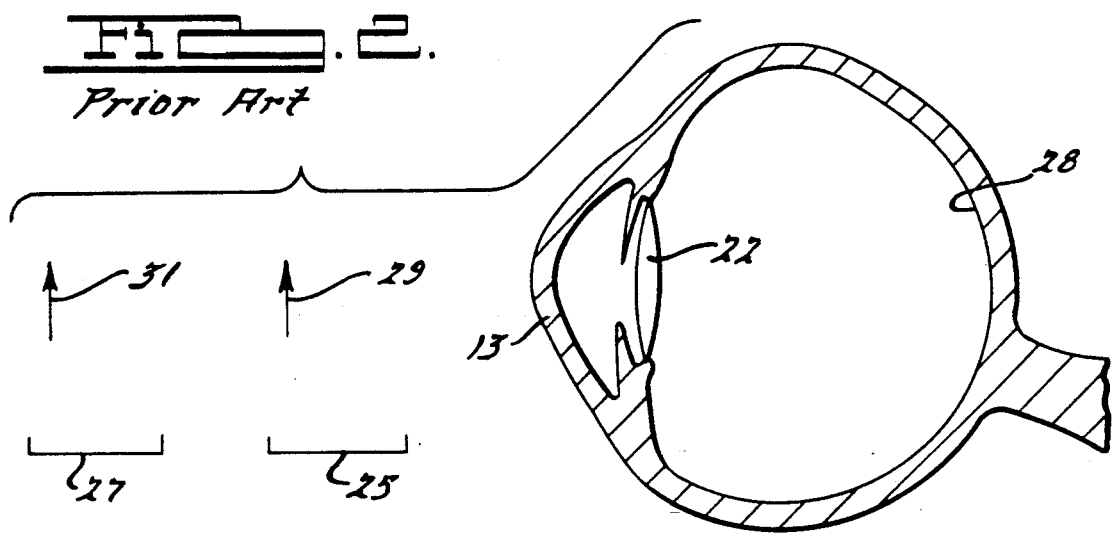
FIG. 2. Prior Art
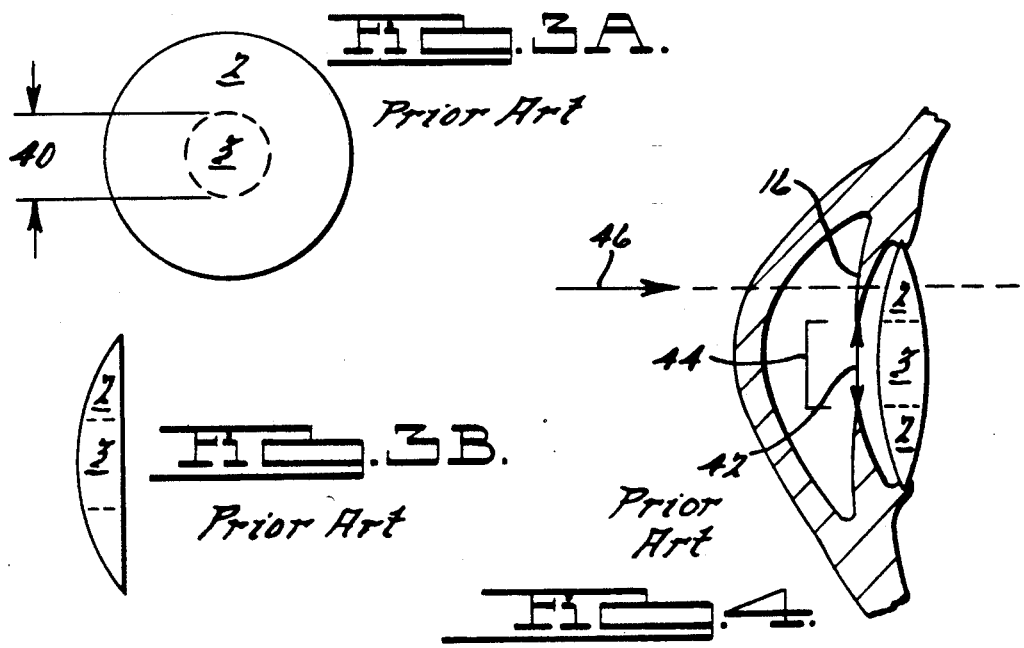
FIG. 3A. Prior Art
FIG. 3B. Prior Art
FIG. 4. Prior Art

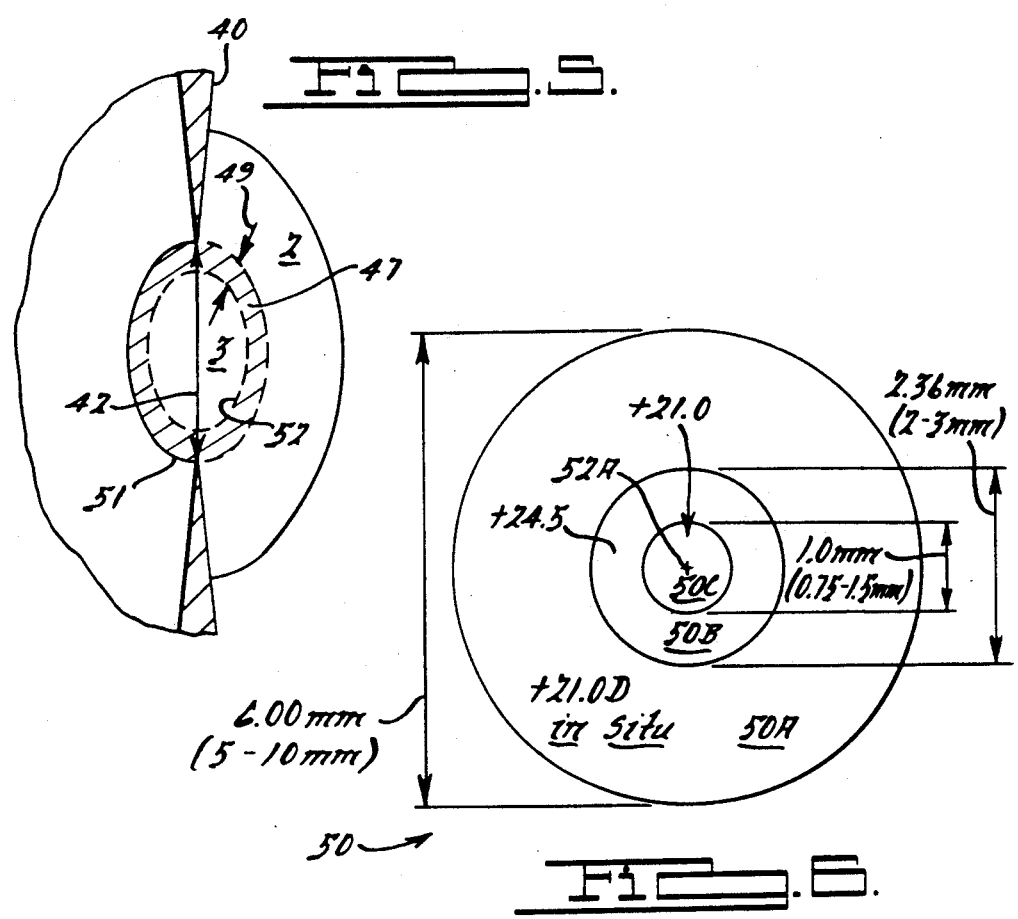
FIG.5.
FIG.6.
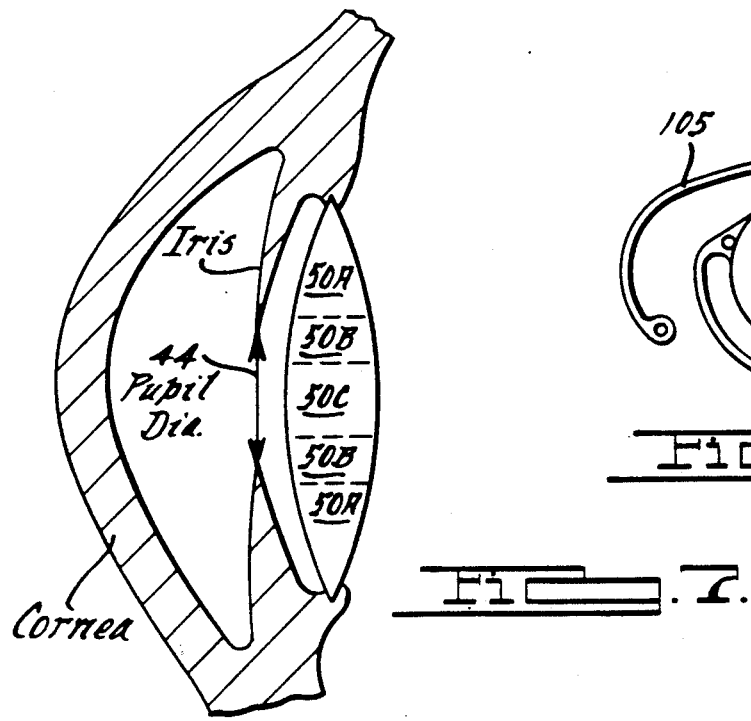
FIG.7.
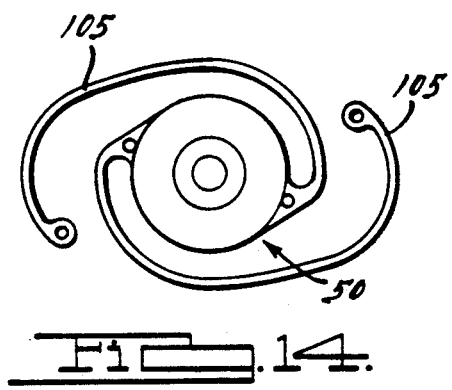
FIG.14.

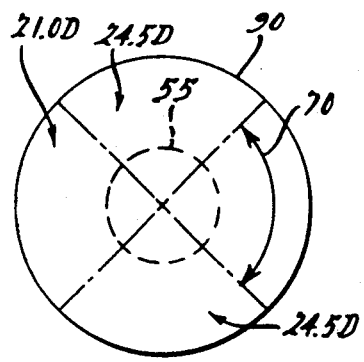 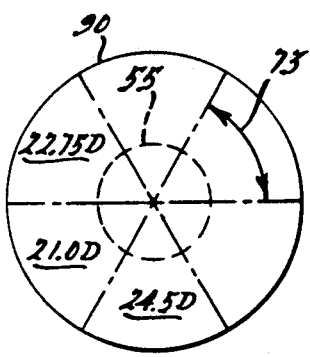 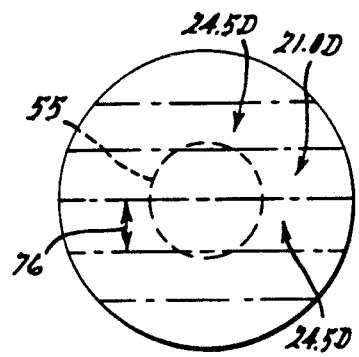
FIG. 8A.   FIG. 8B.   FIG. 8C.
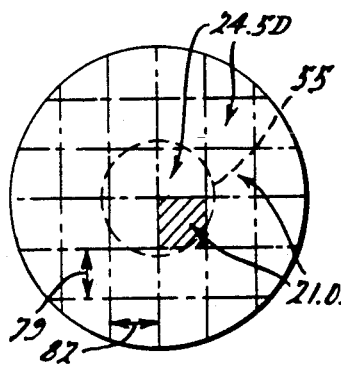 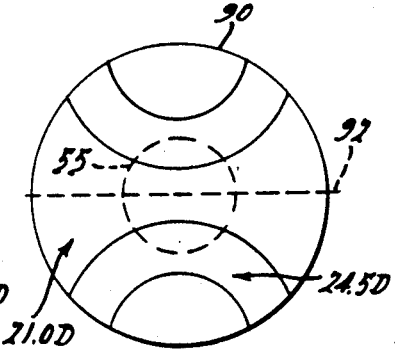 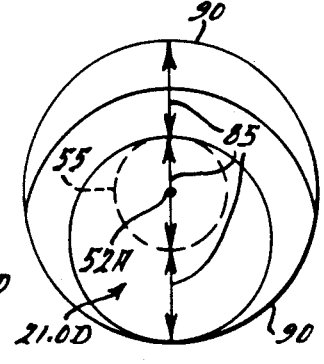
FIG. 8D.   FIG. 8E.   FIG. 8F.
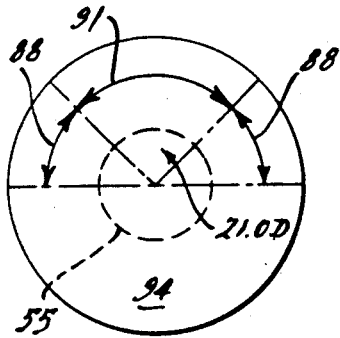 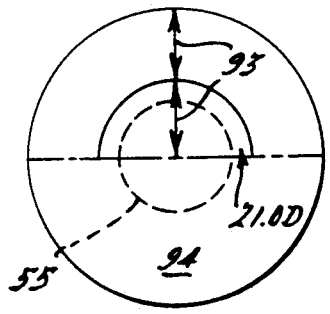 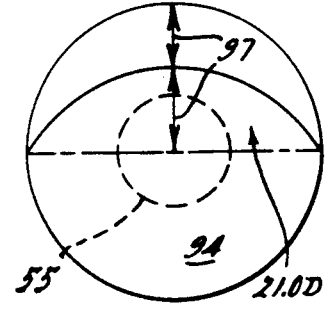
FIG. 8G.   FIG. 8H.   FIG. 8I.
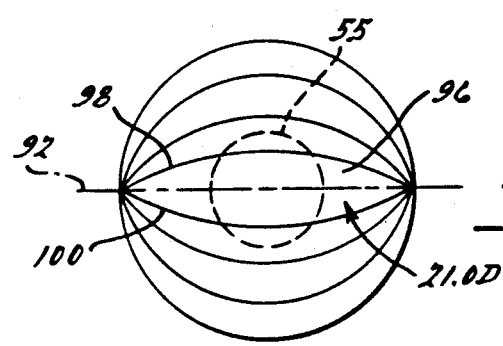
FIG. 8J.

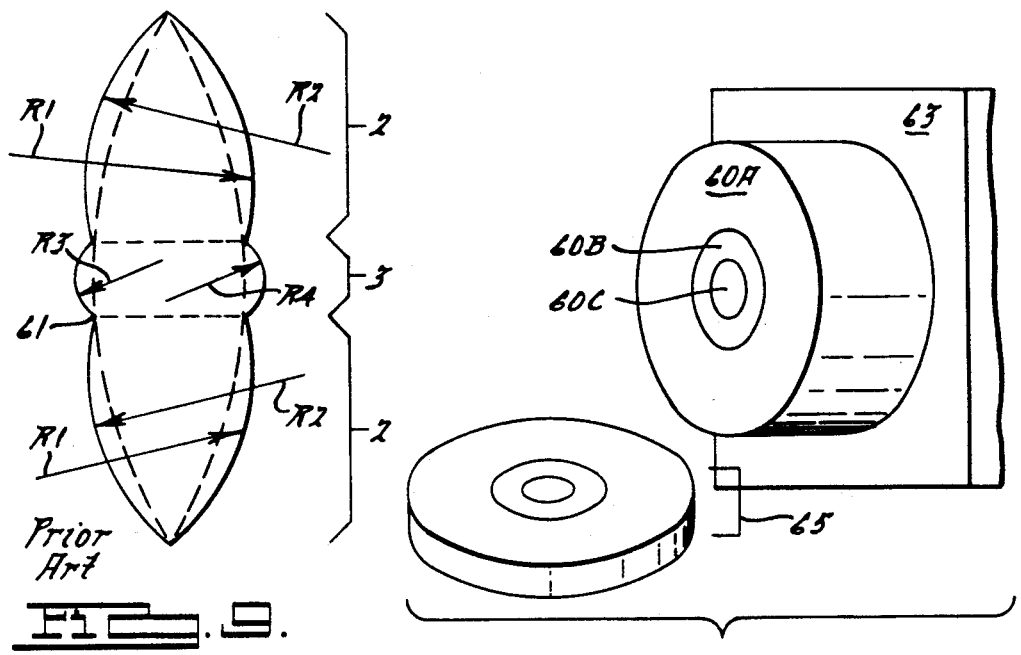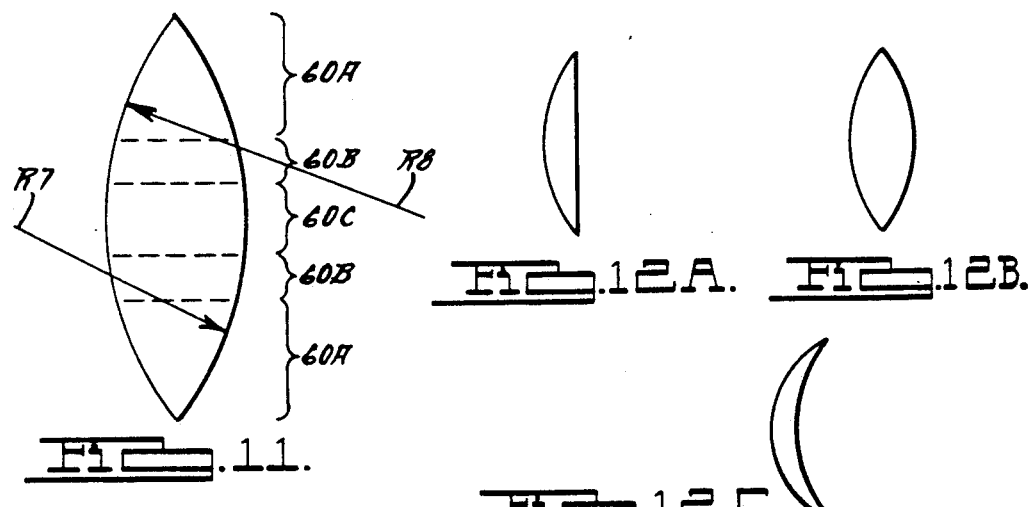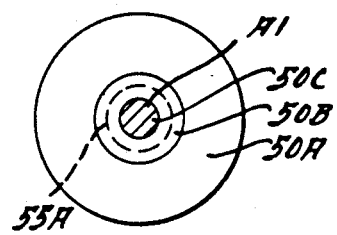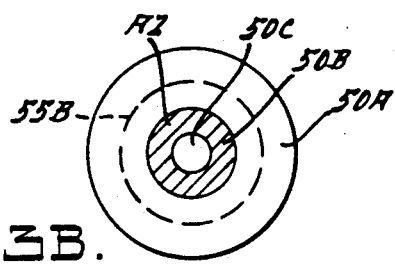

MULTI-FOCAL INTRAOCULAR LENS

The invention relates to intraocular lenses for the human eye and, particularly, to multifocal lenses of this type which can bring images of objects located at different distances into focus on the retina simultaneously.

BACKGROUND OF THE INVENTION

FIG. 1 illustrates a human eye in cross-section, showing cornea 13, iris 16, and lens 19. The lens 19 can suffer disease, such as a cataract, in which case surgical removal of the lens may be necessary. After removal, the lens can be replaced by an artificial lens 22, shown in FIG. 2, and which is termed an intraocular lens (IOL). The IOL restores much of the visual acuity of the eye, but has the characteristic of focusing upon the retina only those objects, such as object 29, which are within the depth of field 25 of the focusing system, which includes the IOL 22 and the cornea 13. Other objects, such as object 31 located in the far field 27, are not in focus, and thus appear blurred.

A prior art device which appears to mitigate this problem is discussed in U.S. Pat. No. 4,636,211 (Nielsen et al.) The Nielsen patent discusses a bifocal IOL as shown in FIG. 3. The Nielsen patent states that "the one piece body has a centrally located optically powered portion for near vision, designated as number 3, which is surrounded by a far vision optically powered portion 2, the two portions being concentric and coaxial."

The Nielsen patent further states that the difference in focusing power between the near vision region 3 and the far vision region 2 should be about 2.50 diopters.

The Nielsen lens, when used as IOL 22 in FIG. 2, focuses both the near-field object 29 and the far-field object 31 simultaneously upon the retina 28. Because the focus of both images differ by 2.50 diopters, the human visual system is able to reject one of the images and view the image which is preferred.

A disadvantage of the Nielsen approach occurs in the presence of bright light. Nielsen states that the diameter 40 in FIG. 3A of the near vision region 3 should be 2.12 millimeters (mm). This diameter is only slightly larger than the diameter 42 in FIG. 4 of the fully constricted pupil 44 of the average human eye when exposed to bright light. In such a situation, the fully constricted pupil prevents adequate incoming light 46 from reaching the far vision region 2 of Nielsen's lens, causing the image of the far field object 31 in FIG. 2 to become very dim on the retina 28. The fully constricted pupil inhibits clear vision of the far field object 31.

Further, even if the pupil does not fully constrict (i.e., the iris 16 does not fully cover Nielsen's far vision region 2 as assumed in the paragraph above), some visual distortion will probably occur. For example, the unblocked, or exposed, part of region 2 of the IOL will resemble annulus 47 in FIG. 5. The annulus 47 is reduced in height, which is indicated by dimension 49, which causes a reduction in cross-sectional area, which, in turn, reduces the amount of light which the annulus can collect.

This reduction in collected light causes the far field image (focused by the annulus) to be less bright than the near field image (focused by region 3). It is believed that this difference in brightness will cause the far field image to be overpowered by the brightness of the near field image, rendering the far field image useless.

The degradation of the far field image just described occurs at a time when objects in the far field are of greatest interest. That is, the bright light, which is responsible for the contraction of the pupil, is generally experienced during outdoor activities, when people are interested in viewing distant objects. However, as just shown, the pupil constriction can obstruct the far-vision region of the IOL and cause distortion or loss of distance vision.

OBJECT OF THE INVENTION

It is an object of the present invention to provide an improved intraocular lens.

It is a further object of the invention to provide an improved intraocular lens which can provide appropriate vision under a wide range of lighting conditions.

It is a further object of the invention to provide an improved intraocular lens which can focus objects at different distances from the eye in which the lens is implanted.

It is a further object of the invention to provide an improved intraocular lens which has bifocal capability, and, further, the ability to focus far field objects in bright light, when the pupil of the eye is constricted.

SUMMARY OF THE INVENTION

In one form of the invention, an intraocular lens contains three concentric regions. An innermost region provides far-field vision. A middle region, surrounding the innermost region, provides near-field vision. An outermost region, surrounding the middle region, provides far-field vision. The innermost region is of a size such that, when the pupil constricts in bright light, the innermost region remains exposed to incoming light, and can thus focus distant images in bright light.

BRIEF DESCRIPTION OF THE DRAWINGS

FIG. 1 illustrates a human eye in cross section.

FIG. 2 illustrates an intraocular lens which can replace the natural lens 19 in FIG. 1.

FIGS. 3A and 3B illustrate a type of bi-focal intraocular lens found in the prior art.

FIGS. 4 and 5 illustrate obstruction of region 2 of the prior art lens of FIG. 3 which occurs when the pupil 44 constricts in bright light.

FIG. 6 illustrates one form of the invention.

FIG. 7 illustrates the invention of FIG. 6 when implanted in the eye.

FIG. 8 illustrates several alternate embodiments of the invention.

FIG. 9 illustrates, in exaggerated form, the lens of FIG. 3A in cross-section.

FIG. 10 illustrates a type of lens blank from which the embodiment of FIG. 6 can be manufactured.

FIG. 11 illustrates the cross-section of a lens manufactured from the blank 65 in FIG. 10.

FIG. 12 illustrates three different types of lens which can be used as the lens of FIG. 6.

FIGS. 13A and 13B illustrate different regions of the lens of FIG. 6 which are exposed under different lighting conditions.

FIG. 14 illustrates a lens of the present invention, including haptic members which are used to support and center the lens in the eye.

DETAILED DESCRIPTION OF THE INVENTION

FIG. 6 illustrates one form of the invention. An intraocular lens 50 contains three regions of focus: 50A, 50B, and 50C. The innermost region 50C has a diameter of 1.00 mm, as indicated. The other two regions, 50B and 50C have respective diameters of 2.36 and 6.00 mm as shown. Two of the regions, namely, regions 50A and 50C, are identical in refractive power at +21.0 diopters, and supply focus for distant vision. The third region 50B is at 24.5 diopters and supplies focus for near vision. (The powers given are measured in aqueous media, not in air, because the lens will be immersed in an aqueous medium in the eye.) All three regions 50A-C are concentric about center point 52A.

When the lens of FIG. 6 is implanted as shown in FIG. 7, imaging of far-field objects is possible despite full constriction of the pupil 44 to the size shown because the central region 50C remains fully exposed. Therefore, distant vision is still available to the patient under bright light conditions. That is, the invention maintains a far field focusing lens (21.0 diopters in the case of region 50C in FIG. 6) within the aperture of the pupil when the iris is fully contracted, that is, when the pupil is at its minimal diameter.

Other configurations in addition to that shown in FIG. 6 can be used. FIGS. 8A-H show ten such configurations. All are 6.00 mm in diameter. A fully constricted pupil is illustrated by dashed circle 55 contained within each figure. Further, as in FIG. 6, zones of different refractive power are labeled, such as 24.5 D, which indicates a refractive power of 24.5 diopters. In addition, dimensions are identified and are explained in the following Table 1, which is considered self-explanatory.

TABLE 1

| Figure | Dimension | Size |
|--------|-----------|------|
| 8A | 70 | 90 degrees |
| 8B | 73 | 60 degrees |
| 8C | 76 | 1.00 mm |
| 8D | 79 | 1.00 mm |
| 8D | 82 | 1.00 mm |
| 8F | 85 | 2.00 mm |
| 8G | 88 | 45 degrees |
| 8G | 91 | 90 degrees |
| 8H | 93 | 1.50 mm |
| 8I | 97 | 1.50 mm |

A particular type of construction of the lens of FIG. 6 will now be discussed. It is common to construct lenses of the Nielsen type by standard methods of grinding and polishing. One such lens is shown in cross-section in grossly exaggerated form in FIG. 9. Far focus regions 2 have radii of curvature R1 and R2 as indicated. Near focus region 3 has different radii, R3 and R4, as further indicated. The lens is not perfectly smooth, as discontinuities exist at points 61 where the radius changes.

The difference in curvature (i.e., R1, in general, does not equal R3) of near vision region 3 as compared with far vision region 2 is necessary because the entire lens is constructed of a single material, such as a polymethyl methacrylate (PMMA), having a single index of refraction.

In an alternate form construction, the lens can be made of more than one material. As shown in FIG. 10, three concentric cylinders 60A-C are co-extruded from a die 63 as known in the art. Cylinders 60A and 60C can be constructed of PMMA or a similar biocompatible material, having a refractive index of 1.491. Cylinder 60B can be constructed of a different material, such as polyallyl methacrylate, having a refractive index of 1.514, or a similar biocompatible material.

A lens blank 65 in the form of a disc is sliced from the extruded cylinders, and ground and polished to the desired shape as shown in cross-section in FIG. 11. This lens, in contrast to the lens of FIG. 9, has only two radii of curvature, namely radii R7 and R8, which can, in some cases, be identical. (If they are identical, then only one radius is said to exist. Further, if one radius is infinite, as in a plano-convex lens, the surface having the infinite radius is flat.) It is the differing indices of refraction of the material in region 60B as compared with that in regions 60A and 60C which provides the different focusing powers in the regions. That is, like the lens of FIG. 6, in the lens of FIG. 10, regions 60A, 60B, and 60C have powers of +21.0, +24.5, and +21.0 diopters, respectively.

Several important features of the invention are the following.

1. The cross-section of the lens can, alternately, be plano-convex as shown in FIG. 12A; bi-convex, as shown in FIG. 12B; or concave-convex (i.e., of the meniscus type), as shown in FIG. 12C. Further, the lens may be manufactured aspherically, in order to correct for spherical or other aberrations.

2. Two different regions of focus (e.g., regions 50C and 50B in FIG. 6, which differ in power by 3.50 diopters) have been considered in the discussion above. However, a greater number of focal regions can be used. For example, in FIG. 6, three, not two, refractive powers can be used: (a) region 50C may be used for far field focus, using a correction of 21.0 diopters, (b) region 50B may be used for a mid field correction of 22.25 diopters, while (c) region 50A may be used for near-field focus, using a correction of 24.5 diopters.

3. In some situations, it can be desirable to construct the lens such that a far field image under bright light conditions is projected onto the retina with the same brightness as a near field image under low light conditions. For example, a given intensity of illumination, I1, of 100 lux, is assumed under the bright light condition, and a second, lower intensity, I2, of 6 lux, is assumed for the low light condition.

It is further assumed that the pupil has a size illustrated by dashed circle 55A in FIG. 13A under the bright light condition and a diameter of dashed circle 55B in FIG. 13B under the low light condition. It is also assumed that region 50C is the region of far field focus, while region 50A is the region of near field focus. In addition, the area of region 50C in FIG. 13A is designated as A1, while the area of region 50B in FIG. 13B is designated as A2.

In this embodiment, the lens is designed such that $(I1) \times (A1) = (I2) \times (A2)$, meaning that bright light intensity (I1) times far focus area (A1) equals low light intensity (I2) times near focus area (A2). This arrangement will provide equal brightness of the near and far field images under bright and low light conditions, because the light intensities per unit area have been equalized for A1 and A2.

4. In the optical art, refractive power, measured in diopters, is generally defined as n/L, wherein n is the refractive index of the medium surrounding a lens and L is the focal length of the lens in air. Thus, one can see that the far-field focusing region 50C in FIG. 6, at 21.0 diopters, has a longer focal length than the near-field region 50B, at 24.5 diopters.

5. FIGS. 8A and 8B show lens regions which are geometric sectors of the circle defined by the periphery 90 of the lens. FIG. 8C shows regions which are parallel bands or stripes. FIG. 8D shows regions occupying the cells in a rectangular gridwork, or chessboard. FIGS. 8E and 8F show regions which are circular, but having centers displaced from the center 52A of the periphery 90. That is, the lens regions are not concentric. Further, FIG. 8E shows a lens which is symmetric about line 92.

FIG. 8G shows regions which are sectors, but not identical. For example, angle 91, subtended by one sector, is about 90 degrees; angles 88 are about 45 degrees; and the lower sector 94 subtends an angle of about 180 degrees. FIGS. 8H and 8I both show a lower sector subtending an angle of 180 degrees. However, in FIG. 8H, the upper section contains two concentric semicircles, while in FIG. 8I the upper section contains crescent-shaped regions. In FIG. 8J, the regions are crescent-shaped and symmetric about line 92. Central region 96 is in the shape of the common area of intersection of two circles, one having circumference 98, and the other having circumference 100. The shape of central region 96 can be called "cat's pupil," because of the resemblance of the shape to the pupil of that animal.

The individual regions shown in FIG. 8 may be spherical lenses or aspheric lenses corrected for aberrations, as discussed above.

In all lenses of FIGS. 8A through 8J, the constricted pupil 55 admits light through a far-field focusing region, such as the hatched region in FIG. 8D having a power of 21.0 D. Similarly, the pupil in FIG. 7 which is constricted to a diameter 44, admits light through far-field focusing region 50C.

6. If the lens should become de-centered upon the eye, the light distribution upon the retina remains substantially unaffected, so long as the amount of de-centering is not too large.

7. It was stated above that the innermost region 50C in FIG. 6 has a diameter of 1.00 mm, the middle region 50B has a diameter of 2.36 mm, and the outer region 50A has a diameter of 6.00 mm. These dimensions fall within the ranges of 0.75-1.50, 2.00-3.00, and 5.00-10.00 mm for the innermost, middle, and outer regions, respectively, and diameters falling within these ranges can be used in the invention.

8. While the IOL of FIGS. 2 and 7 has been shown as positioned in the posterior chamber of the eye, the lens body of the present invention can be implanted in either the posterior or the anterior chamber with techniques commonly known and used in the field today.

Further, although the invention is illustrated in the drawings as being implanted without accompanying haptic members, the lens body, when in use in the eye, is typically combined with a pair, or a greater number, of haptic members for positioning and centering of the lens in the eye. The haptic members can be of any of the sizes and shapes commonly known and used today, such as the Shearing J-loops, the Simcoe C-loops, the Sinsky modified J-loops, etc. For illustrative purposes, an intraocular lens utilizing a lens body 50 of the present invention with a pair of generally J-type loop haptic members 105 is shown in FIG. 14. The haptic members 105 can be affixed to the lens body in any of the methods in common use today, or the lens and haptics can be formed as an integral, one-piece structure.

Numerous substitutions and modifications can be undertaken without departing from the true spirit and scope of the invention as defined in the following claims.

What is desired to be secured by letters patent is the invention as defined in the following claims;

1. An intraocular lens comprising:
   a) a first region, of long focal length, located near the center of the lens, and having a maximum diameter less than the average minimum diameter of a contracted pupil;
   b) a second region, of short focal length, which is substantially concentric about the first region, and having an inner diameter less than the average minimum diameter of a contracted pupil;
   c) a third region, of substantially the same focal length as the first region, and which is substantially concentric about the second region, and having an inner diameter not less than the average minimum diameter of a contracted pupil,
   d) the product of a first predetermined light intensity and the total area of said first region of long focal length located near the center of the lens being substantially equal to the product of a second predetermined light intensity and the total area of said second region of short focal length;
   e) said first predetermined light intensity being greater than said second predetermined light intensity and being about 100 lux; and
   f) said second predetermined light intensity being about 6 lux.

2. A lens according to claim 1 in which the diameter of the first region is in the range of 0.75 to 1.50 millimeters, the outer diameter of the second region is in the range of 2.0 to 3.0 millimeters and the outer diameter of the third region is in the range of 5.00-10.00 millimeters.

* * * * *